United States Patent
Buck et al.

(10) Patent No.: US 11,078,097 B2
(45) Date of Patent: Aug. 3, 2021

(54) PROCESS FOR A FIXED FILM REACTOR AND APPARATUS RELATED THERETO

(71) Applicant: Cambrian Innovation, Inc., Watertown, MA (US)

(72) Inventors: Justin Buck, Auburndale, MA (US); Matthew Silver, Cambridge, MA (US)

(73) Assignee: Cambrian Innovation, Inc., Watertown, MA (US)

( * ) Notice: Subject to any disclaimer, the term of this patent is extended or adjusted under 35 U.S.C. 154(b) by 0 days.

(21) Appl. No.: 16/098,161

(22) PCT Filed: Jun. 15, 2018

(86) PCT No.: PCT/US2018/036158
§ 371 (c)(1),
(2) Date: Nov. 1, 2018

(87) PCT Pub. No.: WO2018/226766
PCT Pub. Date: Dec. 13, 2018

(65) Prior Publication Data
US 2020/0354246 A1    Nov. 12, 2020

Related U.S. Application Data

(60) Provisional application No. 62/628,277, filed on Feb. 8, 2018, provisional application No. 62/569,001, filed (Continued)

(51) Int. Cl.
  *C02F 3/28* (2006.01)
  *C02F 3/00* (2006.01)
(Continued)

(52) U.S. Cl.
  CPC ............. *C02F 3/2893* (2013.01); *C02F 3/006* (2013.01); *C02F 3/2806* (2013.01); *C02F 3/34* (2013.01);
(Continued)

(58) Field of Classification Search
  CPC ...... C02F 3/2893; C02F 3/006; C02F 3/2806; C02F 3/34; C02F 2103/365;
(Continued)

(56) References Cited

U.S. PATENT DOCUMENTS

3,829,377 A * 8/1974 Hashimoato .......... C02F 3/2806
                                                    210/603
4,561,974 A   12/1985 Bernard et al.
(Continued)

OTHER PUBLICATIONS

Sanchez-Hernandez, E.P. et al., "The effect of biogas sparging on cow manure characteristics and its subsequent anaerobic biodegradation", International Biodeterioration and Biodegradation, 83, 2013, pp. 10-16.

*Primary Examiner* — Fred Prince
(74) *Attorney, Agent, or Firm* — Capitol Patent & Trademark Law Firm, PLLC

(57) ABSTRACT

Exemplary embodiments describe apparatuses and related processes for improving mixing and sheer in a fixed film reactor. One process can include recycling at least a portion of a biogas product through at least one sparger below a fixed film zone in the fixed film reactor at conditions sufficient for mixing and sheering the film from an internal structure within the fixed film zone. Often, a cross-sectional area of the fixed film zone fills at least about 90% of a cross-sectional area of the fixed film reactor.

33 Claims, 9 Drawing Sheets

Related U.S. Application Data on Oct. 6, 2017, provisional application No. 62/515,472, filed on Jun. 5, 2017.

(51) Int. Cl.
| | |
|---|---|
| *C02F 3/34* | (2006.01) |
| *C12M 1/107* | (2006.01) |
| *C12M 1/12* | (2006.01) |
| *C12M 1/00* | (2006.01) |
| *C02F 103/36* | (2006.01) |

(52) U.S. Cl.
CPC ............ *C12M 21/02* (2013.01); *C12M 21/04* (2013.01); *C12M 25/00* (2013.01); *C12M 25/14* (2013.01); *C12M 25/18* (2013.01); *C12M 29/06* (2013.01); *C12M 29/24* (2013.01); *C02F 2103/365* (2013.01); *C02F 2203/004* (2013.01); *C02F 2209/008* (2013.01); *C02F 2209/38* (2013.01); *C02F 2303/20* (2013.01); *Y02E 50/30* (2013.01)

(58) Field of Classification Search
CPC .......... C02F 2203/004; C02F 2209/008; C02F 2209/38; C02F 2303/20; C12M 25/18; C12M 29/06; C12M 29/24; C12M 21/02; C12M 25/14; C12M 21/04; C12M 25/00; Y02E 50/30

USPC ................ 210/603, 615, 616, 617, 618, 252
See application file for complete search history.

(56) References Cited

U.S. PATENT DOCUMENTS

| | | |
|---|---|---|
| 5,228,995 A | 7/1993 | Stover |
| 6,569,332 B2 | 5/2003 | Ainsworth et al. |
| 8,580,113 B2 | 11/2013 | Hong et al. |
| 2005/0151281 A1 | 7/2005 | Tharp |
| 2011/0245572 A1 | 10/2011 | Wolf et al. |
| 2012/0132521 A1 | 5/2012 | Silver et al. |
| 2013/0112601 A1 | 5/2013 | Silver et al. |
| 2013/0299400 A1 | 11/2013 | Silver et al. |
| 2013/0319940 A1 | 12/2013 | Josse et al. |
| 2014/0034572 A1 | 2/2014 | McAllister, Jr. |
| 2015/0048024 A1 | 2/2015 | Grelot et al. |
| 2015/0147593 A1 | 5/2015 | Silver et al. |
| 2015/0210575 A1 | 7/2015 | Silver et al. |
| 2016/0023935 A1 | 1/2016 | Josse et al. |
| 2017/0044475 A1 | 2/2017 | Pidaparti et al. |
| 2017/0044573 A1 | 2/2017 | Pidaparti et al. |
| 2017/0044574 A1 | 2/2017 | Pidaparti et al. |
| 2017/0044575 A1 | 2/2017 | Pidaparti et al. |
| 2017/0101612 A1 | 4/2017 | Kleppen et al. |

\* cited by examiner

PROCESS FOR A FIXED FILM REACTOR AND APPARATUS RELATED THERETO

RELATED APPLICATIONS

This application claims priority to U.S. Provisional Applications Nos. 62/515,472 filed Jun. 5, 2017 (the "'472 Application"), 62/569,001 filed Oct. 6, 2017 (the "'001 Application") and 62/628,277 filed Feb. 8, 2018 (the ""277 Application"). This application incorporates by reference the entireties of the '472, '001 and '277 applications as if they were set forth in full herein.

Generally, the present disclosure pertains to a process for fixed film reactors, and an apparatus related thereto.

BACKGROUND

Various reactors are available to treat water, particularly wastewater from municipal, industrial, and agricultural sources. Reactors may contain biomass to aid in treating and removing harmful water contaminants. Some reactors allow the biomass to float freely within the reactor, while others contain internal structures providing a support for biomass growth. The latter, typically called fixed film reactors, suffer from the disadvantage that as the biomass grows; the growth can plug and obstruct the flow of water through the reactor.

During operation, the fixed film reactors can perform as plug flow reactors. Unfortunately, a fixed film reactor may have pockets of dead zones with unmixed water, and thus, the reactor may not have a uniform plug flow profile during operation that can lead to lower conversion and inefficient reactor operations.

Sometimes, monitoring and control of the reactor and support systems from remote locations is desired under a variety of situations. These situations can include, but are not limited to, responding to upset or emergency conditions, operating the equipment by a third party, assisting on-site operations with troubleshooting, conducting troubleshooting for on-site operations, and operating in isolated geographical locations.

Hence, there is a desire to improve the performance of fixed film reactors to overcome the deficiencies discussed above.

SUMMARY

One exemplary embodiment is a process for improving mixing and sheer in a fixed film reactor. The process can include recycling at least a portion of a biogas product through at least one sparger below a fixed film zone in the fixed film reactor at conditions sufficient for mixing and sheering the film from an internal structure within the fixed film zone. Often, a cross-sectional area of the fixed film zone fills at least about 90% of a cross-sectional area of the fixed film reactor.

In embodiments, biomass retention on the media of the fixed film reactor is the mechanism that enables it to function. Accordingly, the amount of shear (force) needs to be at an appropriate level—not too high to avoid excessive removal of biomass, and not too low to allow excessive build-up or accumulation of biomass. In embodiments, gas flow from the sparger(s) may be varied to create varying shear environments. In one embodiment, a higher level of gas flow may be provided to increase shear stress to remove biomass as needed, while in another embodiment a low level of gas flow may be provided to provide mixing within the reactor without disrupting biomass adhesion to the fixed film on the media.

In embodiments, biogas may be drawn from the top (head space) of reactor's tank, or from another location, and fed to one or more spargers underneath the fixed film zone to re-cycle the biogas. In embodiments, the biogas can be conveyed or otherwise transported from a collection location (e.g., head space) by one or more means, including, but not limited to fan(s), blower(s), pump(s), compressor(s), or venturi apparatuses, for example.

The process can further include that the internal structure has a static packing media, and the static packing media may have a permeable working electrode, counter electrode, and insulating spacer material. Generally, the working electrode, the counter electrode, and the insulating spacer material may have, independently, a flat planar shape. Moreover, the fixed film zone can include a dynamic packing media, in turn, may include inert supports. Sometimes, a cross-sectional area of the fixed film zone fills at least 99% of a cross-sectional area of the fixed film reactor. The process may further include a manifold coupled to the at least one sparger for communicating the at least a portion of the biogas product underneath the fixed film zone. Typically, the biogas product has at least about 50% or even at least about 95%, by mole, methane. Additionally, the fixed film zone can include one or more methanogenic bacteria. Further, the process may include providing a feed having wastewater to the fixed film reactor.

Alternatively, the biological gas used for sparging, may contain predominantly nitrogen gas ($N_2$) and carbon dioxide ($CO_2$) and may not contain significant amounts of methane. For example, a gas may contain up to 99% nitrogen gas or as low as 1% nitrogen gas. In embodiments, the gas used for sparging must not contain significant levels of oxygen in order to maintain an anaerobic reactor environment (e.g. oxygen levels in the sparge gas must remain below 1%). As such, the sparge gas may not be air.

Another exemplary embodiment is an apparatus for generating a biogas. The apparatus can include a reactor at a first location, a manifold within the reactor, at least one sparger coupled to the manifold, at least one sensor for detecting one or more conditions within the apparatus, at least one transmitter in communication with the at least one sensor for transmitting data detected by the sensor, and at least one receiver at a second location for receiving a signal with transmitted data from the first location where the second location is remote from the first location. Typically, the reactor contains one or more microbes for converting a feed into a biogas.

In one exemplary embodiment, the reactor of the apparatus includes a fixed film zone. Optionally, the manifold and at least one sparger is underneath the fixed film zone. Usually, the at least one sparger has a disk sparger. Often, the fixed film zone has one or more methanogenic bacteria. The fixed film zone can include a working electrode, a counter electrode, and an insulating spacer material, and the working electrode, the counter electrode, and the insulating spacer material may be permeable. Sometimes, the working electrode, the counter electrode, and the insulating spacer material are orientated horizontally and stacked in the fixed film zone.

In additional embodiments, a sparger may comprise a multi-zone sparger, where each zone is connected to a separate manifold and configured to allow a different flow rate of the re-cycled gas to be distributed to a different section of the reactor. For example, it may be desirable to periodically provide a high level of gas flow to one section to facilitate removal of solids from the media above that section while maintaining low (or lower) levels of a gas flow rate to the remaining sections that does not remove solids from a media but is at a rate that allows for appropriate mixing to avoid undisturbed pockets in the wastewater, for example. Additionally, a plurality of anaerobic reactors, each having its own sparge zones, may be provided. In such an embodiment, a single re-cycled gas conveyance and distribution system may be provided. Alternatively, multiple conveyance and distribution systems may be provided within a single anaerobic reactor, or some combination of the above. In embodiments, various conveyance systems may be sized to different flow rates to achieve different purposes (e.g. mixing or removal), and either may be controlled to operate continuously or intermittently.

Still further, embodiments of the invention may include: (1) an anaerobic fixed film reactor comprising, a fixed film packing media configured within a zone of a reactor and to allow biological media (e.g., methanogenic bacteria) to anchor and grow, wherein a cross-sectional area of the zone fills at least about 90% of a cross-sectional area of the reactor; a manifold for receiving re-cycled biogas; a plurality of spargers coupled to the manifold and configured for distributing the re-cycled biogas to wastewater below the fixed film packing media.

Further, in additional embodiments, an inventive reactor may include spargers that are further configured to: (i) output biogas at a flow rate ranging from 0.1 to 10 cubic meter per hour per square meter of a reactor, horizontal cross-section area for providing turbulence of the wastewater and avoiding the formation of undisturbed pockets of the wastewater, and/or (ii) output biogas at a flow rate ranging from 1 to 100 cubic meter per hour per square meter of a reactor, horizontal cross-section area for creating shearing on the packing media to prevent clogging of the media.

The spargers may be configured to underlie the fixed film packing media.

In embodiments, the fixed film packing media may comprise: (a) a static packing media, or (b) a dynamic packing media.

In embodiments, the biogas may comprise (i) methane, by volume or by mole, of about 50% to about 85%, (ii) methane, by volume or by mole, of about 95%, (iii) one or more of carbon dioxide, hydrogen sulfide, and heavy hydrocarbons, or (iv) nitrogen gas and carbon dioxide gas, and less than 1% oxygen gas.

The present invention further provides embodiments one or more of the spargers may comprise a multi-zone sparger, where each zone of the multi-zone sparger is connected to a separate manifold and configured to allow a different flow rate of the re-cycled gas to be distributed to a different sub-zone of the reactor.

Exemplary reactors provided by the present invention may yet further include a controller for controlling the biogas flow rate into the spargers, and a transmitter for transmitting a signal indicating an amount of the re-cycled biogas.

In addition to the exemplary reactors just described, the present invention may include a number of related processes. For example, one exemplary process may include a process for distributing re-cycled biogas in an anaerobic fixed film reactor comprising: allowing biological media (e.g., methanogenic bacteria) to anchor and grow on a fixed film packing media configured within a zone of a reactor, wherein a cross-sectional area of the zone fills at least about 90% of a cross-sectional area of the reactor; receiving re-cycled biogas at a manifold; and distributing the re-cycled biogas to wastewater from a plurality of spargers coupled to the manifold and configured below the fixed film packing media.

Such a process may further include outputting biogas at a flow rate ranging from 0.1 to 10 cubic meter per hour per square meter of a reactor, horizontal cross-section area to provide turbulence of the wastewater and avoiding the formation of undisturbed pockets of the wastewater, and/or outputting biogas at a flow rate ranging from 1 to 100 cubic meter per hour per square meter of a reactor, horizontal cross-section area create shearing on the packing media to prevent clogging of the media.

Similar to before, in such a process the biogas may comprise: (i) methane, by volume or by mole, of about 50% to about 95%, or (ii) nitrogen gas and carbon dioxide gas, and less than 1% oxygen gas.

These and other features and advantages will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DEFINITIONS

Figure 1:
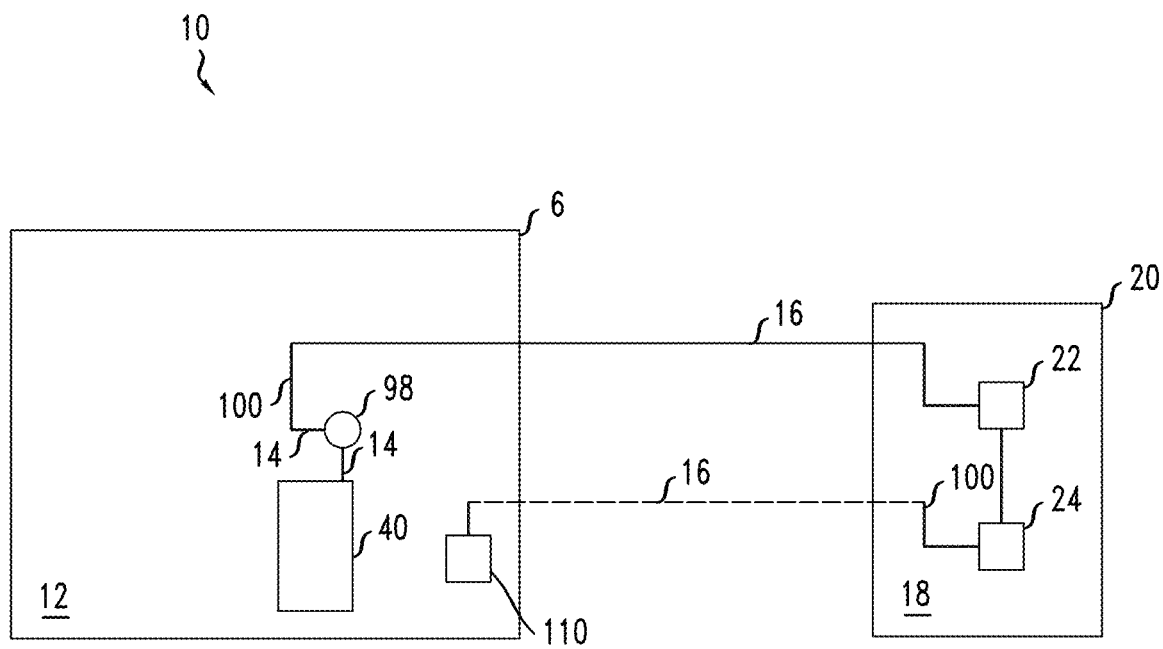
FIG. 1 is a schematic view of an exemplary apparatus.

As used herein, the words "comprising", and any form thereof such as "comprise" and "comprises"; "having", and any form thereof such as "have" and "has"; "including", and any form thereof such as "includes" and "include"; and "containing" and any form thereof such as "contains" and "contain" are inclusive or open-ended and do not exclude additional, unrecited elements or process steps.

As used herein, the term "stream" can include various molecules in liquid or gas state, and can include mixtures of gases, liquids, and particulate solids. Generally, a stream can be a wastewater stream or a biogas stream containing methane.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones. The word "section" may be used interchangeably with the word "zone".

As depicted, process flow lines in the figures can be referred to interchangeably as, e.g., lines, pipes, feeds, portions, products, or streams.

As used herein, the term "about" or "approximately" is defined as being close to or near as understood by one of ordinary skill in the art, and in some embodiments may be quantified as within 10%, more particularly within 5%, still more particularly within 1%, and is in some cases within 0.5%.

As used herein, the term "a" or "an" when used in conjunction with the term comprising or a form thereof may mean "one", but is also consistent with the meaning of "one or more", "at least one", and "one or more than one".

As used herein, the term "hour" may be abbreviated "hr", the term "kilogram" may be abbreviated "kg", the term "Pascal" may be abbreviated "Pa", the term "milligram" may be abbreviated "mg", the term "liter" may be abbreviated "L", the term "meter" can be abbreviated "m", the terms "meter-cubed" may be abbreviated "$m^3$", the terms "biological oxygen demand" may be abbreviated "BOD", the terms "chemical oxygen demand" may be abbreviated "COD", and the terms "degrees Celsius" may be abbreviated "° C.". All pressures are absolute.

As used herein, the term "coupled" can mean two items, directly or indirectly, joined, fastened, associated, supported, connected, attached, or formed integrally together either by chemical, electrical, or mechanical means, by processes including stamping, molding, or welding. What is more, two items can be coupled by the use of a third component such as a mechanical fastener, e.g., a screw, a nail, a staple, or a rivet; an adhesive; or a solder. It should also be understood that one or more exemplary embodiments may be described as a process or method. Although a process/method may be described as sequential, it should be understood that such a process/method may be performed in parallel, concurrently or simultaneously. In addition, the order of each step within a process/method may be re-arranged. A process/method may be terminated when completed and may also include additional steps not included in a description of the process/method.

As used herein, the term "and/or" includes any and all combinations of one or more of the associated listed items.

It should be understood that where used herein, the designations "first", "second", "third", etc., is purely to distinguish one component (e.g., app, device, subsystem, section, etc.,) or part of a process from another and does not indicate an importance, priority or status. In fact, the component or parts of a process could be re-designated (i.e., re-numbered) and it would not affect the scope of the present invention.

As used herein the phrases "connection", "connected to", or similar phrases means an indirect or direct physical connection between at least two different parts of a device or system or means one part of a device or system is subsumed within (and thereby connected to) at least one other part of a device or system. It should be understood that when one part of a device or system is described or depicted as being connected to another part, other components used to facilitate such a connection may not be described or depicted because such components are well known to those skilled in the art.

Yet further, when one part of a device or system is described or depicted as being connected to another part using "a connection" (or single line) in a figure it should be understood that practically speaking such a connection (line) may comprise (and many times will comprise) more than one physical connection or channel, may be omni-directional or bi-directional, and may or may not include separate data, formatting and signaling.

It should be noted that the systems and devices, as well as any subsystems, etc., thereof, illustrated in the figures are not drawn to scale, are not representative of an actual shape or size and are not representative of any actual system, platform or device layout, or manufacture's drawing. Rather, the systems and devices are drawn so as to help explain the features, functions and processes of various exemplary embodiments of the present invention described herein.

As used herein, the term "embodiment" refers to one example of the present invention.

DETAILED DESCRIPTION

Exemplary embodiments of anaerobic fixed film reactors and related methods are described herein. It should be understood that, although specific exemplary embodiments are discussed herein, there is no intent to limit the scope of the present invention to such embodiments. To the contrary, it should be understood that the exemplary embodiments discussed herein are for illustrative purposes, and that modified and alternative embodiments may be implemented without departing from the scope of the present invention. Said another way, the exemplary embodiments presented herein are only some of the many that fall within the scope of the present invention, it being practically impossible for the inventor to describe all of the many possible exemplary embodiments and variations that fall within the scope of the present invention.

Further, it should be understood at the outset that although an exemplary implementation of at least one embodiment of the present disclosure is illustrated below, the present system may be implemented using any number of techniques, whether currently known or in existence. The present disclosure should in no way be limited to the exemplary implementations, drawings, and techniques illustrated below, including the exemplary design and implementation illustrated and described herein, but may be modified within the scope of the appended claims along with their full scope of equivalents.

Generally, exemplary processes for utilizing internally generated biogas for an anaerobic fixed film reactor are disclosed. These processes provide sufficient turbulence and recirculation to create an uplift effect and minimize dead zones (i.e., undisturbed, un-mixed liquid) within the reactor. As such, the reactor can model a continuously stirred tank model during continuous sparging or a batch operation during intermittent sparging, thereby yielding a higher conversion. The embodiments herein can also provide sufficient sheer conditions within the reactor to remove excessive biomass growth to prevent plugging and clogging of the reactor and aid in regulating biofilm accumulation. Such operations minimize maintenance and repair downtimes and improve overall reactor performance. In addition, the embodiments herein can provide remote monitoring and control over the unit to provide flexibility when equipment is provided by third party contractors or operations are conducted at remote locations.

Referring to FIG. 1, an exemplary apparatus 10 can include a facility 6 at a first location 12 and an offsite facility 20 at a second location 18. Generally, the facility 6 can be a wastewater treatment facility, a chemical or petrochemical manufacturing facility, or an agricultural waste processing plant. The facility 6 can include a reactor 40, as hereinafter described, that can include the at least one instrument 98 and at least one transmitter 100. Communication links 14 can facilitate data transfer from the reactor 40 to the at least one instrument 98, and in turn, to the at least one transmitter 100. The at least one transmitter 100 can send a signal 16 containing the data to a receiver 22 at the offsite facility 20. The offsite facility 20 can be an office of a contractor or provider of the first location 12, a headquarters for the first location 12, or another manufacturing facility of the facility 6 at the first location 12. Generally, the offsite facility 20 is remote from the facility 6, and the locations 12 and 18 can be separated by a mile, 10 miles, 100 miles, or even a thousand or more miles. The receiver 22 can transmit the received data to a computer 24 for analysis and determine modifications of operating parameters of the reactor 40. Exemplary data can include compositional analysis, pH, pressure, and temperature of fluid, e.g., gas and/or liquid streams, and flow rates, and determinations of volatile fatty acids and biological oxygen demand of the treated wastewater. As a further example, the amount of biogas production, e.g., methane production, can be transmitted and used for accounting purposes. Moreover, the reactor 40 efficiency can be ascertained by measuring the amount or absence of recycled biogas. An instruction or signal 16 can be transmitted by a transmitter 100 in communication with the computer 24 and sent back to the first location 12 to a controller 110 being adapted for receiving signals. The controller 110 can make modifications in the operating equipment, such as pumps, heat exchangers, furnaces, valves, and/or the reactor 40 for adjusting operations of the reactor 40. Typically, the controller 110 sends one or more signals to one or more control valves 120 to modify operating conditions, as discussed when referring to FIG. 2.

Figure 2:
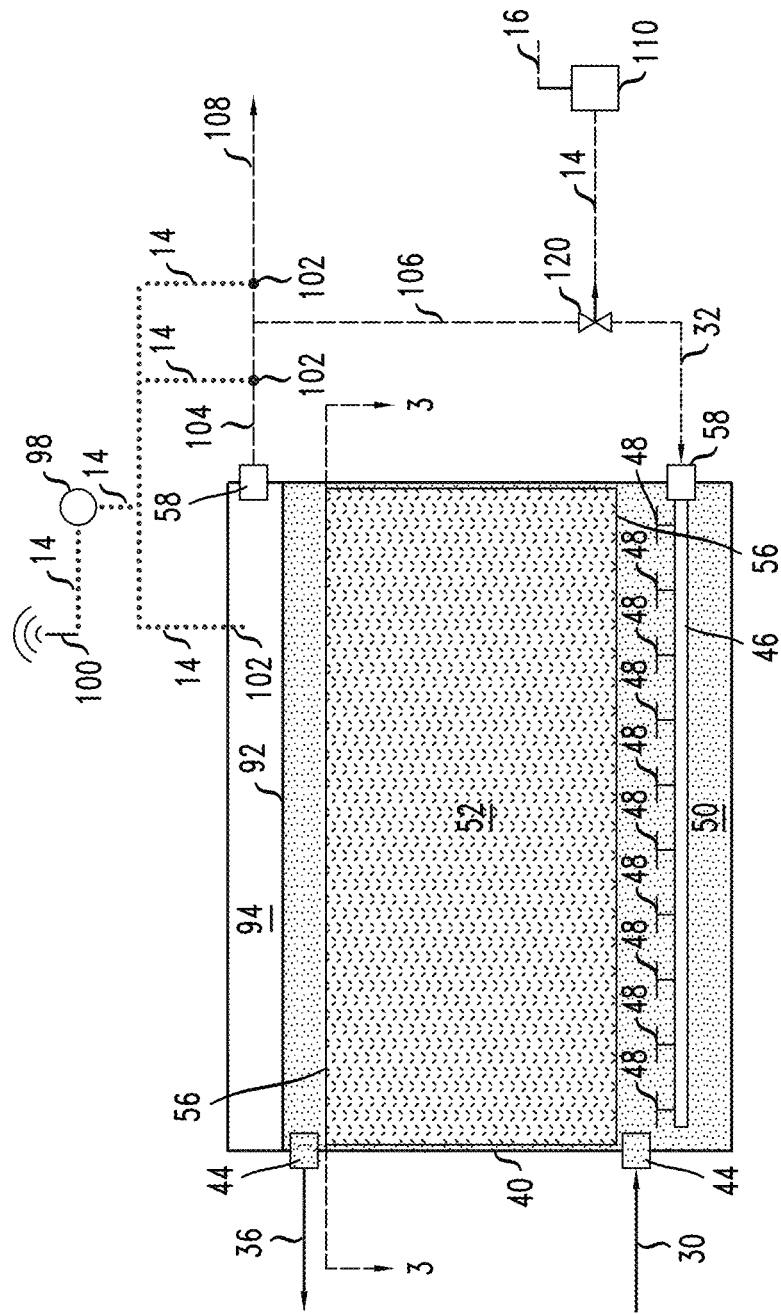
FIG. 2 is an elevational, cross-sectional view of an exemplary reactor.

Referring to FIG. 2, the reactor 40 can include liquid inlet/outlets 44, a manifold 46, at least one sparger 48, a liquid zone 50, a fixed film zone 52, an internal structure 56, gas inlet/outlets 58, at least one instrument 98, a controller 110, and a control valve 120. The liquid inlet 44 and outlet 44 are, respectively, a liquid introduction nozzle and removal nozzle. The gas inlet and outlet 58 are, respectively, a gas introduction nozzle and a gas removal nozzle. Compared to membrane bioreactors, one of the goals of the fixed film reactor is to maintain a biofilm attached to the internal components. As a result, the gas flow must not remove all biomass. Thus, one or more manifolds 46, each including a plurality of pipes may underly the fixed film zone 52 to provide an appropriate amount of mixing and/or shear within the reactor 40. At least one diffuser or sparger 48 can be coupled to the manifold 46. In this view, ten disk spargers 48 are depicted, but it should be understood that additional rows of spargers can extend depth wise into the figure to underlie the fixed film zone 52. Moreover, different types of spargers may be used instead of or in addition to the spargers in this exemplary embodiment. In some exemplary embodiments, at least about 20, even about 50, or even as much as at least 100 spargers may be used to underlie the fixed film zone 52 to provide sufficient conditions for mixing and sheering. In embodiments, the size of bubbles produced by a sparger 48 may range in size from small (fine), to large (coarse) to very large (balloon). For example, fine bubbles may range in size from 0.1 mm to 3 mm, coarse bubbles may range from 3 mm to 30 mm and "balloon" bubbles may be in excess of 30 mm up to 1000 mm.

In embodiments, a sparger 48 may be configured as a disc, ball, sphere, tube, a flat sheet or panel, for example.

Exemplary spargers 48 are disclosed in, e.g., US 2005/0151281 A1. Often, the internal structure 56 defines the fixed film zone 52 with internal supports at the upper and lower boundary of the fixed film zone 52 and includes solid components within the fixed film zone 52.

Generally, the fixed film zone 52 contains materials or structures, typically fixed or limited in movement, to facilitate the growth of biological media. In contrast, other systems prohibit or minimize the growth of biological media on materials or structures within the reactor. As an example, a membrane bioreactor contains a membrane for separating free-growth biological material from water, but often prohibits or minimizes biological growth on structures, including the membrane, within the reactor. In embodiments of the invention, the amount of mixing and shearing may be controlled to optimize the growth of biological growth, minimize the formation of undisturbed pockets of wastewater but, at the same time, avoid clogging of the media.

In additional embodiments, a sparger 48 may comprise a multi-zone sparger (not shown in figures), where each zone includes a separate manifold. In embodiments, each separate manifold may be configured and operable to allow a different level of gas flow (flow rate) to be distributed to a different section or sub-zone of the fixed film reactor. For example, it may be desirable to periodically provide a high level of gas flow to one sub-zone of the reactor to facilitate removal of solids from media above that sub-zone while maintaining low (or lower) levels of a gas flow rate to the remaining sub-zones that does not remove solids from a media but is at a rate that allows for appropriate mixing to avoid undisturbed pockets in the wastewater, for example. Additionally, a plurality of anaerobic reactors, each having its own sparge sub-zones or sections, may be provided. In such an embodiment, a single re-cycled gas conveyance and distribution system may be provided. Alternatively, multiple conveyance and distribution systems may be provided within a single anaerobic reactor, or some combination of the above. In embodiments, various conveyance systems may be sized to different flow rates to achieve different purposes (e.g. mixing or removal), and either may be controlled to operate continuously or intermittently.

Figure 3:
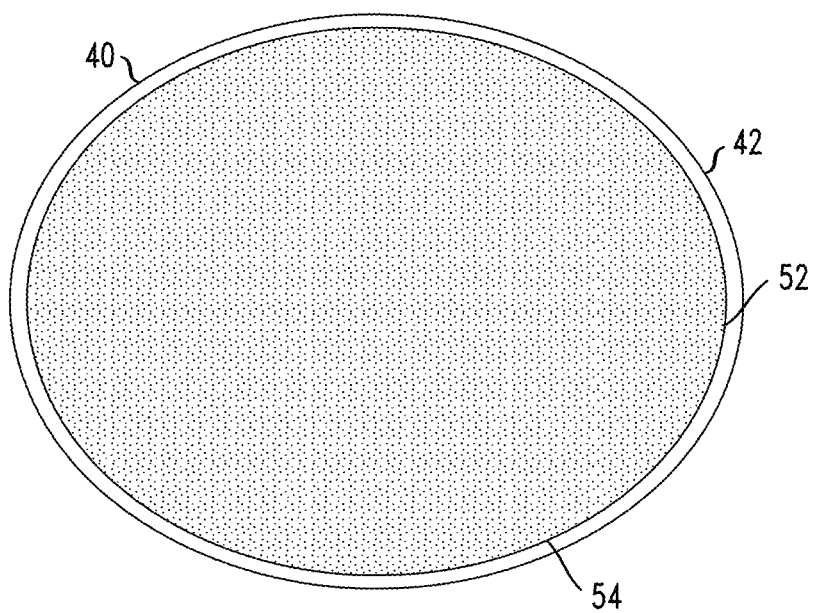
FIG. 3 is a cross-sectional view along lines 3-3 of FIG. 2 of the exemplary reactor.

Referring to FIG. 3, a cross-sectional view depicts a cross-sectional area 54 of the fixed film zone 52 as compared to the cross-sectional area 42 of the reactor 40. Generally, the cross-sectional area 54 of the fixed film zone 52 fills at least about 90%, about 95%, or even about 99% of the cross-sectional area 42. In other exemplary embodiments, the fixed film zone 52 can be a chamber within the reactor 40. Thus, the fixed film zone 52 can encompass almost the entire diameter of the reactor 40.

The fixed film zone 52 can include any suitable static or dynamic packing media. The packing media provides a fixture for a film or biological media to anchor and grow. The biological media can include any micro-organism or microbe, such as one or more bacteria, archaea, and/or yeast, suitable to treat the entering wastewater, including a methanogenic microbe. In one exemplary embodiment, the fixed film zone 52 may include one or more methanogenic bacteria, such that the fixed film zone 52 can be utilized for anaerobic digestion processes. Examples of suitable methanogenic microbes include, but are not limited to, species of *Methanobacterium, Methanosarcina, Methanococcus*, and *Methanospirillum*. Such microbes are disclosed in, e.g., US 2013/0299400 A1. In addition to micro-organisms or microbes found commonly in other wastewater treatment systems, in another exemplary embodiment a fixed-film reactor with bio-electrochemical electrodes may include electrically active microbes which transfer electrons to or from the electrodes. These microbes can include, but are not limited to, species of *Geobacter, Pseudomonas*, and *Shewanella*.

Usually, anaerobic digestion uses microbial species that occupy different niches, roughly divided into two groups based on their metabolisms. The acid-former group, which contains many sub-niches, includes species that digest polysaccharides, sugars, fatty acids, alcohols and more complex molecules in the waste into organic acids, primarily acetate, but also others like lactate and butyrate. Typically, the second class is the methane-formers, or methanogens, which may include two sub-niches. Some methanogens can metabolize acetate directly and produce methane as a byproduct (aceticlastic methanogenesis), while other methanogenic species may combine $H_2$ as an electron donor with $CO_2$ to produce methane (hydrogenotrophic methanogenesis).

Although not wanting to be bound by theory, in aceticlastic methanogenesis, for each molecule of acetate consumed, often equal amounts of carbon dioxide and methane are produced. In hydrogenotrophic methanogenesis, for every four molecules of hydrogen gas consumed, typically one molecule of carbon dioxide is also consumed to produce methane and two molecules of water. Generally, while aceticlastic methanogenesis produces carbon dioxide, the hydrogenotrophic process effects a net decrease in carbon dioxide. A discussion of anaerobic digestion is disclosed in, e.g., US 2013/0299400 A1.

Figure 4:
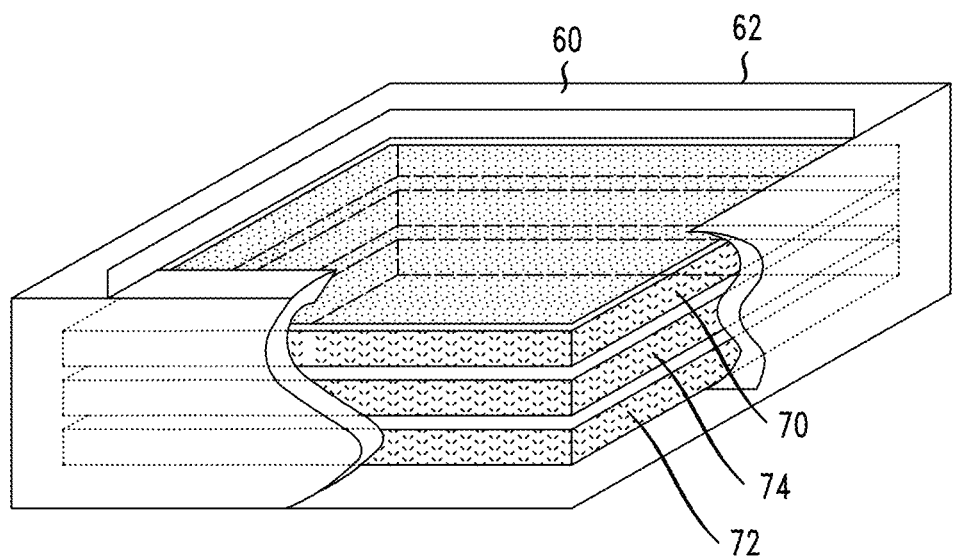
FIG. 4 is a perspective, cutaway view of an exemplary static packing media.
Figure 5:
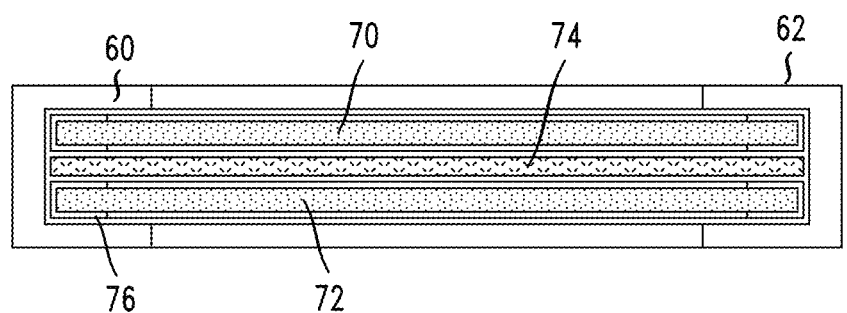
FIG. 5 is an elevational, cross-sectional view of the exemplary static packing media.

Referring to FIGS. 4-5, an exemplary static packing media 60 can have the form of a module 62. The static packing media 60 can include a working electrode 70, a counter electrode 72, and insulating spacer material 74. The static packing media 60 can optionally include an electrode frame components 76. In some exemplary embodiments, the working electrode 70 can be an anode and the counter electrode 72 may be a cathode, and in other exemplary embodiments the working electrode 70 can be a cathode and the counter electrode 72 can be an anode. Usually, the fixed film zone 52 includes numerous modules 62 powered by an electrical source. Alternatively, the module 62 can take form of several, repeating layers orientated horizontally and stacked extending across most of the diameter of the reactor 40. Optionally, these layers can have a flat planar shape. These layers can take the form of a mesh and be permeable allowing fluids to pass there-through. In embodiments, components configured as planar shaped (e.g., electrodes, spacer material, etc.,) may be further configured to be oriented either horizontally or vertically such that wastewater may flow past or through the planar shaped component.

The anode and cathode of each anode/cathode pair can be made of the same material or different materials. Suitable materials include, but are not limited to, biochar, graphite granules, stainless steel, wire mesh, carbon mesh, carbon cloth, carbon fiber, carbon felt, or carbon granules, or a combination thereof. As an example, the anode in at least one of the anode/cathode pairs can be made of a carbon material, such as carbon mesh, carbon cloth, carbon fiber, or carbon felt, while the cathode is stainless steel (e.g., a stainless-steel mesh). Alternatively, the anode in at least one of the anode/cathode pairs can be stainless steel (e.g., a stainless-steel mesh), while the cathode is made of a carbon material such as carbon mesh, carbon cloth, carbon fiber, or carbon felt. In certain embodiments, the anode and/or the cathode are made from two or more materials. As a further example, the anode and/or cathode can be made from a combination of stainless steel and carbon mesh, carbon cloth, carbon fiber, or carbon felt, or a combination of wire mesh and carbon mesh, carbon cloth, carbon fiber, or carbon felt.

The anode and cathode in each of the anode/cathode pairs can be separated by a porous, insulating layer (e.g., a plastic material). The porous, insulating layer that separates the anode and cathode can also be used to support the anode and cathode in the pairing. As yet another example, the anode and cathode can be painted onto either side of a porous, insulating layer. Optionally, a filter can be included, such as a filter made from biochar, graphite granules, or activated carbon.

As discussed above, water and/or a gas flow upwards through the anode/cathode assembly. In certain embodiments, the anode and the cathode in each of the two or more anode/cathode pairs are arranged such that water and/or gas flows upwards through an anode, then a cathode in each of the anode/cathode pairs. Exemplary modules are disclosed in, e.g., US 2015/0147593 A1. It should be understood, however, that though embodiments herein are described as being configured to provide water flow in an upwards direction, that additional embodiments may be provided were flow is in a downwards direction. That is to say, flow within the reactor may be in any direction. Still further, in an alternative embodiment, the flow of water (or other liquids) may alternate from upwards to downwards in space (e.g., anaerobic baffled reactor) or in time (e.g. in a sequenced batch operation). Yet further, the present invention provides for different flow directions for routine operation, maintenance and cleaning. For instance, a liquid up flow configuration may be used during routine operation, while liquid downflow may be used in combination with high rates of biogas sparging during periodic cleaning and maintenance cycles.

Other exemplary static packing media include bio-filters, bio-scrubbers, and bio-trickling filters. Usually, bio-filters utilize biofilms growing on solid support media such as compost or simple foam cubes that often double as a nutrient source. Typically, bio-scrubbers utilize a two-stage solution in which a gas is first absorbed into a liquid and then reacted by bacteria growing in a liquid phase. Generally, bio-trickling filters utilize bacteria immobilized on a rigid support media, such as rock or activated carbon, over which water and nutrients are trickled. Each of these approaches has benefits and costs disclosed US 2013/0299400 A1.

Figure 6:
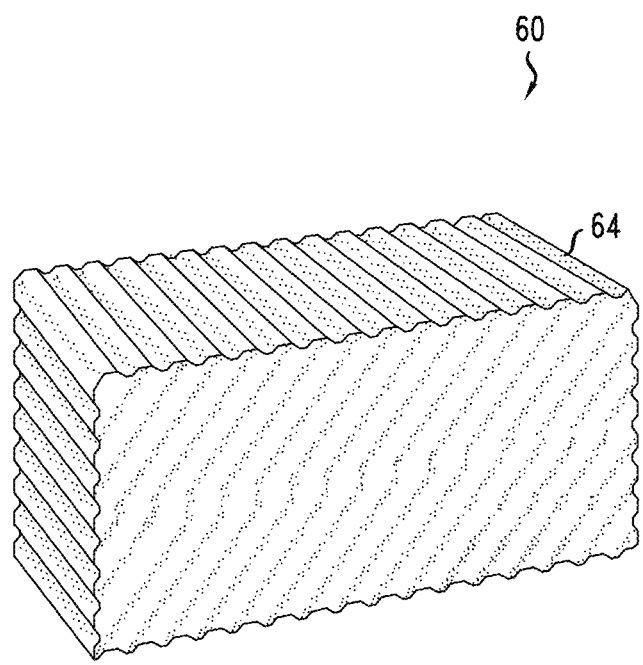
FIG. 6 is a perspective view of another exemplary static packing media.

Referring to FIG. 6, another exemplary static packing media 60 is depicted. In this exemplary embodiment, the static packing media 60 can have the form of a block 64 with grooves and recesses to facilitate the growth of biological material. Multiple blocks 64 can be prearranged in the reactor 40 before operations.

Figure 7:
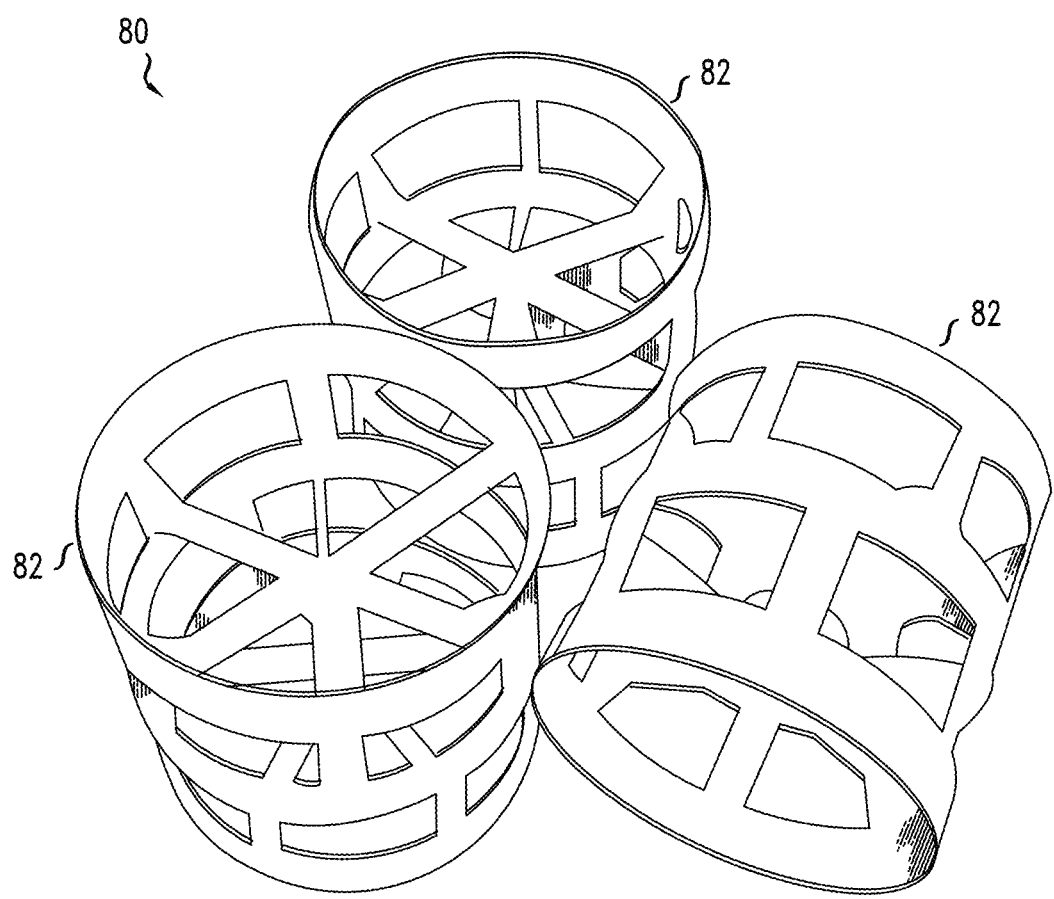
FIG. 7 is a perspective view of exemplary dynamic packing media.

Referring to FIG. 7, a dynamic packing media 80 can take the form of numerous inert supports 82. The inert supports 82 can take any suitable form, such as rings or cages, which generally increases the surface area for biological material to anchor thereto. Typically, the inert supports 82 can be fabricated from any suitable nonsoluble material, such as metal, ceramic, carbon, or plastic. The inert supports 82 are not fixed, but are loose within the reactor 40, but can be bounded by screens incorporated into the internal structure 56. Typically, such inert supports 82 are dumped into the reactor 40 prior to operations. Exemplary inert supports 82 are disclosed in, e.g., U.S. Pat. No. 4,561,974.

Although the exemplary reactor 40 has been described above, it should be understood that other reactor designs could be utilized, including those disclosed in U.S. Pat. No. 4,561,974, and other designs than fixed film reactors. Further, the dynamic media 80 may be used as a part of a number of different anaerobic water treatment reactor configurations including, but not limited to, an anaerobic filter, an anaerobic moving bed bioreactor, an anaerobic fluidized bed reactor, and an anaerobic baffled reactor, for example.

Referring back to FIG. 2, in operation, generally a feed 30 is provided to the liquid inlet 44 and collects in the bottom of the reactor 40 below the fixed film zone 52 in a liquid zone 50. Often, the feed 30 is a wastewater stream from a residential, agricultural, and/or industrial source. Typically, a recycled stream 32, usually containing biogas and described in further detail below, passes the inlet 58 and into the manifold 46. The biogas can pass through the spargers 48 mix with the wastewater below the fixed film zone 42 and provide turbulence and shearing action within the reactor 40. In this manner, the flow of fluid upwards with pockets of turbulence through the reactor can model a continuously stirred tank reactor for continuous sparging or a batch operation for intermittent sparging and avoid the formation of undisturbed pockets. Generally, the treated liquid passes upwards through the fixed film zone 52 and the packing media contained therein. Usually, the packing media has fixed film bacteria thereon where the organic compounds are digested or degraded. During this process, biogas is generated, which often consists substantially of methane and carbon dioxide. The treated water accumulates above the fixed film zone 52 at a level 92. Excess liquid can pass through the outlet 44. Optionally, at least a portion of the excess liquid can be recirculated to the liquid zone 50 (not shown).

Concurrently, biogas can pass through the packing media and accumulate in the head space 94 of the reactor 40. In embodiments, biogas may be re-cycled from the head space 94 (or another area or section of the reactor) by drawing the biogas from the top head space 94 and feeding it to one or more spargers 48 underneath the fixed film zone. In embodiments, the biogas can be conveyed or otherwise transported from the head space 94 by one or more means, including, but not limited to fan(s), blower(s), pump(s), compressor(s), or venturi apparatuses, for example, in conjunction with controller 110 via outlet 58 as a biogas product stream 104.

In embodiments, the amount of biogas flowing into a sparger 48 or from a zone of a sparger 48 into a reactor sub-zone (flow rate) at a particular time period may be controlled manually or automatically. For example, the biogas flow rate from a collection location into the spargers 48 may be controlled using the controller 110, The controller 110 may be operable to store control instructions as electrical signals in a memory, where the instructions may generate signals that are exchanged with blowers, fans, pumps, valves that are connected to the controller 110 in order to vary the speed of such devices or change their operation (e.g., open, close a valve) or otherwise change the pressure profile of the gas delivery system in order to vary or change the biogas flow rate into a sparger or sparger sub-zone 48. By controlling the biogas flow rate into a sparger or sparger sub-zone 48, the controller 110 may control the biogas flow rate into a sub-zone of the reactor as well.

Further, the controller 110 may be connected to a flow meter that is operable to measure the flow rate of the biogas. Based on signals the controller 110 receives from the flow meter, the controller 110 may send signals to pumps, fans, blowers and valves, etc., to vary the flow rate of biogas transported from the head space 94 to the sparger(s) 48 or sparger sub-zones.

Typically, the biogas includes at least about 50%, about 55%, about 85%, or even about 95%, by volume or by mole, methane. The biogas may also include carbon dioxide, nitrogen gas (i.e. molecular nitrogen or dinitrogen, $N_2$), hydrogen sulfide, and heavier hydrocarbons, such as propane.

Alternatively, the biologically re-cycled gas used for sparging, may contain predominantly nitrogen gas ($N_2$) and carbon dioxide ($CO_2$) and may not contain significant amounts of methane. For example, a re-cycled gas may contain up to 99% nitrogen gas or as low as 1% nitrogen gas. In embodiments, the re-cycled gas used for sparging must not contain significant levels of oxygen in order to maintain an anaerobic reactor environment (e.g. oxygen levels in the sparge gas must remain below 1%). As such, the sparge gas may not be air.

Generally, the reactor 40 is a fixed film reactor and can operate at a temperature of about 5-about 85° C., a pressure of about 100,000-about 200,000 Pa, a pH of about 5-about 9, a recirculation flow rate of about 15-about 35 $m^3$/hr, and a sparge gas flow rate of about 20-about 50 $m^3$/hr. Typically, the reactor 40 produces a biogas product that has at least about 55% methane, by volume, and a methane yield of at least about 250 L/kg total COD. However, it should be understood that the recirculation flow rate of the liquid and gas may vary. Further, in embodiments flow rates and superficial velocities may be coupled through the cross-sectional area of the flow path. Accordingly, because the cross-sectional flow area may vary dramatically depending upon the reactor design (size, and shape) the recirculation flow rates may also change dramatically.

In embodiments, the amount of liquid flow per cross-sectional area may vary from 0.1 m3/hr per m2 to 100 m3/hr per m2, while the amount of gas flow per cross-sectional area may depend on the liquid flow and the desired degree of mixing and/or biomass removal. As indicated previously lower gas flow rates, ranging from 0.1 m3/hr per m2 to 10 m3/hr per m2, may be used to facilitate mixing, for example, while higher gas flow rates, ranging from 1 m3/hr per m2 to 100 m3/hr per m2, may be used to facilitate excess biomass removal.

Accordingly, in embodiments of the invention, the spargers 48 may be configured to output biogas at a biogas gas flow rate ranging from 0.1 to 10 cubic meter per hour per square meter of a reactor, horizontal cross-section area for providing turbulence of the wastewater and avoiding the formation of undisturbed pockets of the wastewater.

In addition, the spargers 48 may be configured to output biogas at a biogas gas flow rate ranging from 1 to 100 cubic meter per hour per square meter of a reactor, horizontal cross-section area for creating shearing on the packing media to prevent clogging of the media.

The biogas can pass through the gas outlet 58 as a biogas product 104. At least a portion 106 of the biogas product 104 can be recycled. Generally, the recycled biogas stream 106 with a fixed flow rate improves the mixing in the reactor 40 so that the internal structure 56 and packing media therein are more accessible to bacteria; and to shear off the excessive biomass. At least a portion 108 of the biogas product 104 can be further treated, stored, or burned in, e.g., a central heat and power system.

Optionally, the biogas product 104 can be treated to remove contaminants such as hydrogen sulfide. Any suitable process can be utilized to remove hydrogen sulfide, such as adsorption or biological treatment solutions. Such processes are disclosed in, e.g., US 2013/0299400 A1. The biogas product 104 can be treated or conditioned to reduce hydrogen sulfide levels to an amount suitable for recycling to the reactor 40 and/or for use in downstream processes, such as fuel for a boiler system or a central heat and power system. Typically, the biogas product 104 is treated to lower hydrogen sulfide content to no more than about 100 ppm, or even about 10 ppm, by volume, hydrogen sulfide. The biogas product 104 can also be further compressed for recycling and/or downstream operations. Desirably, compression is minimized and for recycling purposes can depend on the height of the reactor 40. Generally, the recycled biogas stream 106 is at a pressure of no more than about 310,000 Pa, no more than about 170,000 Pa, or even about 130,000- about 170,000 Pa. Additionally, the biogas product 104 can be compressed to be delivered to a plurality of reactors for sparging and/or fuel for other process operations.

Referring to FIGS. 1 and 2, the at least one instrument 98 can include several sensors 102 for measuring several process parameters, such as temperature, pH, pressure, flow rates, and stream compositions. These sensors 102 may include one or more flow meters, pressure gauges, temperature gauges, compositional analyzers, and pH measurement probes. Measured process parameters can include: temperature, pH, flow rate, pressure, liquid level, stream composition, and electrode electrical function. The electrode electrical function may be represented by a wide range of electrical properties including, but not limited to, voltage, potential, current, capacitance, inductance, resistance, impedance, or properties determined from electrochemical activity, including, but not limited to polarization curves, linear sweep voltammetry, cyclic voltammetry, electrical impedance spectroscopy, and chronoamperometry.

Usually, the acquired data is transferred via communication links 14 to the at least one instrument 98 and passes to a communication link to a transmitter 100. The transmitted data can be sent to an offsite facility 20 for processing and analysis, as described above. The offsite facility 20 can transmit signals providing remote control of controllers, such as control valves, pumps, compressors, and other equipment to change operating parameters of the reactor 40. As an example, the flow of the recycled biogas product stream 106 can be regulated with the control valve 120 receiving a signal 16 via the controller 110 and the communication link 14. The signal 16 to the controller 110 can originate from the offsite facility 20. Thus, the flow of the recycled biogas stream 106 can be regulated remotely depending on conditions within the reactor 40, the treated wastewater stream 36, and/or the biogas product 104.

EXAMPLES

The following examples are intended to further illustrate the subject process. These illustrations of embodiments are not meant to limit the claims to the particular details of these examples. These examples are based on engineering calculations and actual operating experience with similar processes.

Figure 8:
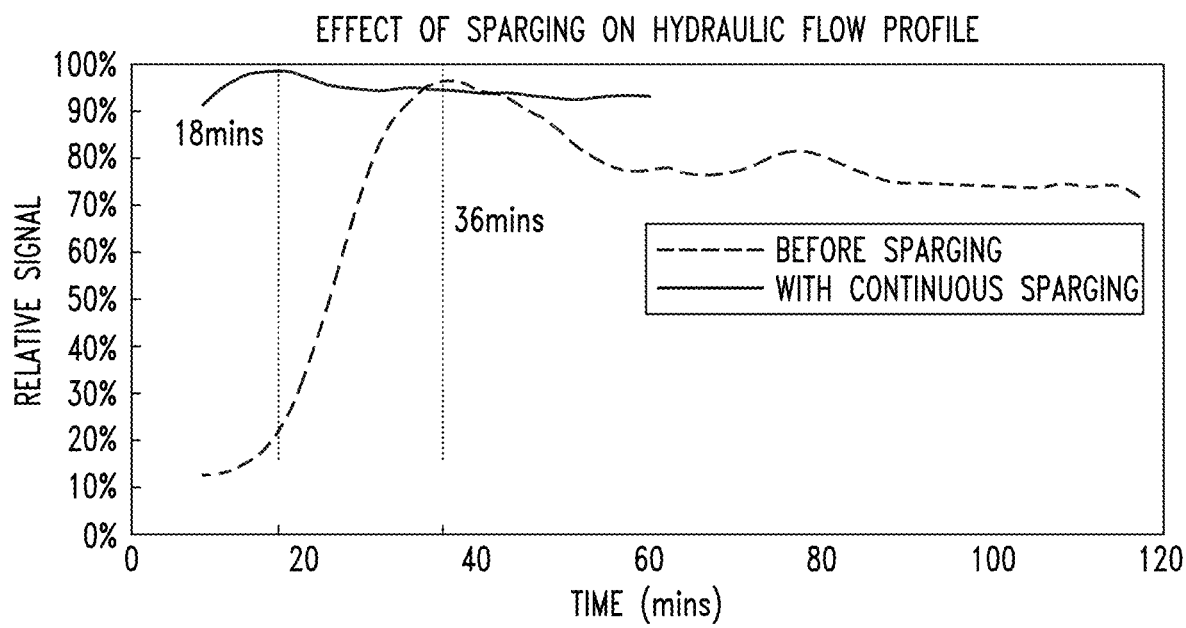
FIG. 8 is a graphical depiction of relative signal versus time.

Plant tests are conducted with tracers for two trials. The tracer tests are conducted on a full industrial scale anaerobic fixed film reactor before biogas sparging, and with continuous biogas sparging. The liquid volume is 72 m$^3$, the recirculation flow rate for the first three trials is 18 m$^3$/hr and for the fourth trial is 26 m$^3$/hr. Results are also depicted graphically in FIG. 8.

The gas sparging changes the flow profile as demonstrated by the hydraulic tracer test. Without gas sparging the reactor operates with a pronounced peak retention which indicates a dominance of plug flow characteristics, and with gas sparging the tracer profile more closely resembles a well-mixed system.

Figure 9:
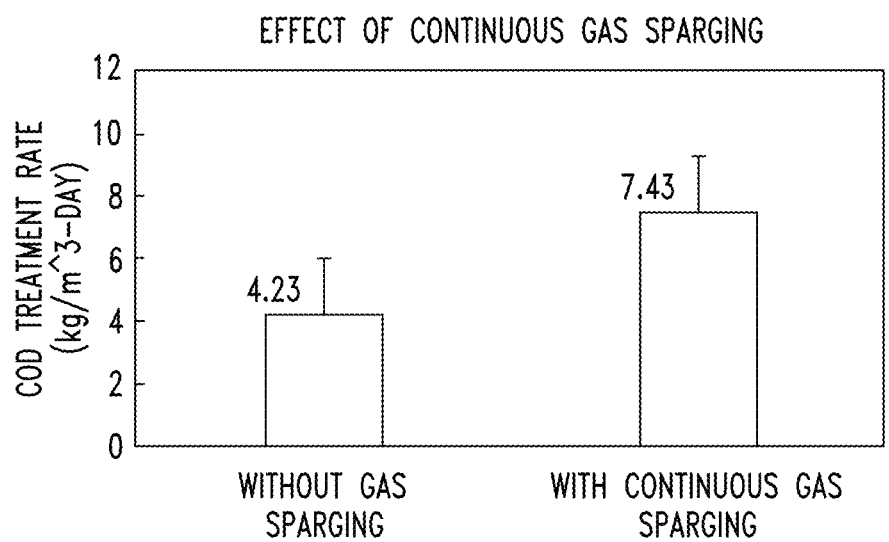
FIG. 9 is a bar graph depiction of COD treatment rate with and without continuous gas sparging.

In another trial, a high rate biogas sparging facilitates mixing and decreases the presence of hydraulic dead zones within the reactor. As depicted in FIG. 9, the result is a substantial increase in the performance of the system with COD treatment rates increasing about 75%. Particularly, the COD treatment rate is 4.23 kg/m$^3$-day without gas sparging and the COD treatment rate is 7.43 kg/m$^3$-day with gas sparging.

Figure 10:
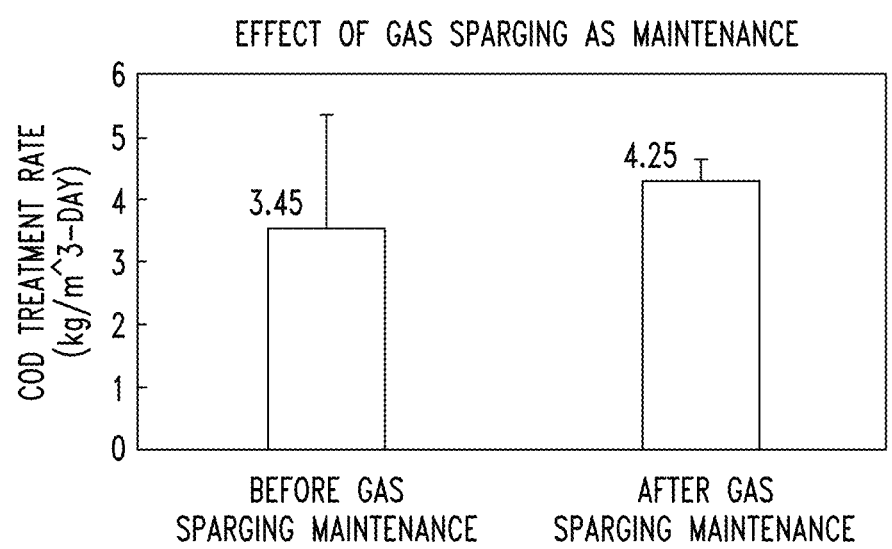
FIG. 10 is a bar graph depiction of COD treatment rate with and without continuous gas sparging as maintenance.

Likewise, a high rate gas sparging removes excess biological accumulation in a fixed film reactor. As depicted in FIG. 10, the result is a restoration of peak operating treatment rates following the intermittent maintenance sparging. Before gas sparging maintenance is 3.45 kg/m$^3$-day and after gas sparging maintenance is 4.23 kg/m$^3$-day. The results after sparging are also more consistent, as represented by the smaller variance (standard deviation) within the sample set.

Thus, a reactor experiencing low treated wastewater output due to excessive solids, as well as poor mixing due to hydraulic dead zones, can benefit from reactor sparging. Reactor performance data demonstrates that with biogas sparging, the reactor recovers 90% of its maximum treatment rates achieved before system failure. However, if biogas sparging stops, system performance starts to decline. Therefore, the results suggest that biogas sparging is an effective method for operating anaerobic fixed film reactors for improved mixing and excessive solids removal.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

From the foregoing description, one skilled in the art can easily ascertain the essential characteristics of this invention and, without departing from the spirit and scope thereof, can make various changes and modifications of the invention to adapt it to various usages and conditions. For example, one or more components shown in the figures and/or described in the text herein may be integrated into a single treatment vessel or into separate treatment vessels (see for example, how the components are separated in the '001 and '277 applications).

The scope of the invention sought to be protected by the inventors is set forth in the claims that follow and any equivalents of such claims.

We claim:
1. An anaerobic fixed film reactor comprising:
   a fixed film packing media configured within a zone of a reactor and to allow biological media to anchor and grow, wherein a cross-sectional area of the zone fills at least about 90% of a cross-sectional area of the reactor;
   a manifold for receiving re-cycled biogas; and
   a plurality of spargers coupled to the manifold and configured for distributing the re-cycled biogas to wastewater below the fixed film packing media, wherein the spargers are further configured to output biogas at a flow rate ranging from 0.1 to 10 cubic meter per hour per square meter of a reactor, horizontal cross-section area for providing turbulence of the wastewater and avoiding formation of undisturbed pockets of the wastewater.
2. The reactor as in claim 1 wherein the spargers are further configured to underlie the fixed film packing media.
3. The reactor as in claim 1 wherein the fixed film packing media comprises a static packing media.

4. The reactor as in claim 1 wherein the fixed film packing media comprises a dynamic packing media.

5. The reactor as in claim 1 wherein the biological media comprises methanogenic bacteria.

6. The reactor as in claim 1 wherein the biogas comprises methane, by volume or by mole, of about 50% to about 85%.

7. The reactor as in claim 1 wherein the biogas comprises methane, by volume or by mole, of about 95%.

8. The reactor as in claim 1 wherein the biogas comprises one or more of carbon dioxide, hydrogen sulfide, and heavy hydrocarbons.

9. The reactor as in claim 1 further comprising a transmitter for transmitting a signal indicating an amount of the re-cycled biogas.

10. The reactor as in claim 1 wherein one or more of the spargers comprises a multi-zone sparger, where each zone of the multi-zone sparger is connected to a separate manifold and configured to allow a different flowrate of the re-cycled biogas to be distributed to a different sub-zone of the reactor.

11. The reactor as in claim 1 wherein the biogas comprises nitrogen gas and carbon dioxide gas, and less than 1% oxygen gas.

12. The reactor as in claim 1 further comprising a controller for controlling the biogas flow rate into the spargers.

13. A process for distributing re-cycled biogas in an anaerobic fixed film reactor comprising:
 allowing biological media to anchor and grow on a fixed film packing media configured within a zone of a reactor, wherein a cross-sectional area of the zone fills at least about 90% of a cross-sectional area of the reactor;
 receiving re-cycled biogas at a manifold;
 distributing the re-cycled biogas to wastewater from a plurality of spargers coupled to the manifold and configured below the fixed film packing media; and
 outputting biogas at a flow rate ranging from 0.1 to 10 cubic meter per hour per square meter of a reactor, horizontal cross-section area to provide turbulence of the wastewater and avoiding formation of undisturbed pockets of the wastewater.

14. The process as in claim 13 wherein the biological media comprises methanogenic bacteria.

15. The process as in claim 13 wherein the biogas comprises methane, by volume or by mole, of about 50% to about 95%.

16. The process as in claim 13 wherein the biogas comprises nitrogen gas and carbon dioxide gas, and less than 1% oxygen gas.

17. An anaerobic fixed film reactor comprising:
 a fixed film packing media configured within a zone of a reactor and to avow biological media to anchor and grow, wherein a cross-sectional area of the zone fills at least about 90% of a cross-sectional area of the reactor;
 a manifold for receiving re-cycled biogas; and
 a plurality of spargers coupled to the manifold and configured for distributing the re-cycled biogas to wastewater below the fixed film packing media, wherein the spargers are further configured to output biogas at a flow rate ranging from 1 to 100 cubic meter per hour per square meter of a reactor, horizontal cross-section area for creating shearing on the packing media to prevent clogging of the media.

18. The reactor as in claim 17 wherein the spargers are further configured to underlie the fixed film packing media.

19. The reactor as in claim 17 wherein the fixed film packing media comprises a static packing media.

20. The reactor as in claim 17 wherein the fixed film packing media comprises a dynamic packing media.

21. The reactor as in claim 17 wherein the biological media comprises methanogenic bacteria.

22. The reactor as in claim 17 wherein the biogas comprises methane, by volume or by mole, of about 50% to about 85%.

23. The reactor as in claim 17 wherein the biogas comprises methane, by volume or by mole, of about 95%.

24. The reactor as in claim 17 wherein the biogas comprises one or more of carbon dioxide, hydrogen sulfide, and heavy hydrocarbons.

25. The reactor as in claim 17 further comprising a transmitter for transmitting a signal indicating an amount of the re-cycled biogas.

26. The reactor as in claim 17 wherein one or more of the spargers comprises a multi-zone sparger, where each zone of the multi-zone sparger is connected to a separate manifold and configured to allow a different flowrate of the re-cycled biogas to be distributed to a different sub-zone of the reactor.

27. The reactor as in claim 17 wherein the biogas comprises nitrogen gas and carbon dioxide gas, and less than 1% oxygen gas.

28. The reactor as in claim 17 further comprising a controller for controlling the biogas flow rate into the spargers.

29. A process for distributing re-cycled biogas in an anaerobic fixed film reactor comprising:
 allowing biological media to anchor and grow on a fixed film packing media configured within a zone of a reactor, wherein a cross-sectional area of the zone fills at least about 90% of a cross-sectional area of the reactor;
 receiving re-cycled biogas at a manifold;
 distributing the re-cycled biogas to wastewater from a plurality of spargers coupled to the manifold and configured below the fixed film packing media; and
 outputting biogas at a flow rate ranging from 1 to 100 cubic meter per hour per square meter of a reactor; horizontal cross-section area to create shearing on the packing media to prevent clogging of the media.

30. The process as in claim 29 further comprising outputting biogas at a flow rate ranging from 1 to 100 cubic meter per hour per square meter of a reactor, horizontal cross-section area to create shearing on the packing media to prevent clogging of the media.

31. The reactor as in claim 29 wherein the biological media comprises methanogenic bacteria.

32. The reactor as in claim 29 wherein the biogas comprises methane, by volume or by mole, of about 50% to about 95%.

33. The reactor as in claim 29 wherein the biogas comprises nitrogen gas and carbon dioxide gas, and less than 1% oxygen gas.

* * * * *